US006664442B2

(12) United States Patent
McConlogue et al.

(10) Patent No.: US 6,664,442 B2
(45) Date of Patent: Dec. 16, 2003

(54) SELECTING COMPOUNDS TO REDUCE INFLAMMATION ASSOCIATED WITH ALZHEIMER'S DISEASE

(75) Inventors: Lisa C. McConlogue, Burlingame, CA (US); Kate D. Games, Belmont, CA (US); Theodore A. Yednock, Forest Knolls, CA (US); Tan Hua, Daly City, CA (US); Elizabeth Messersmith, El Cerrito, CA (US); Frederique Bard, Pacifica, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 09/823,549

(22) Filed: Mar. 30, 2001

(65) Prior Publication Data

US 2002/0147998 A1 Oct. 10, 2002

Related U.S. Application Data

(60) Provisional application No. 60/193,847, filed on Mar. 30, 2000.

(51) Int. Cl.[7] ........................ G01N 33/00; A01K 67/00; A01K 49/00

(52) U.S. Cl. ............................... 800/3; 800/12; 800/18; 424/9.2

(58) Field of Search ................................ 800/8, 12, 13, 800/14, 18, 3; 424/9.2

(56) References Cited

FOREIGN PATENT DOCUMENTS

| | | | |
|---|---|---|---|
| WO | WO 96/06927 | A1 | 3/1996 |
| WO | WO 96/09857 | A1 | 4/1996 |
| WO | WO 96/40896 | A1 | 12/1996 |

OTHER PUBLICATIONS

Games et al., "Alzheimer–type neuropathology in transgenic mice overexpressing V717F β–amyloid precursor protein," *Nature,* 373:523–527 (1995).

Hsiao et al., "Correlative Memory Deficits, Aβ Elevation, and Amyloid Plaques in Transgeneic Mice," *Science,* 274:99–102 (1996).

Sturchler–Pierrat et al., "Two amyloid precursor protein transgenic mouse models with Alzheimer disease–like pathology," *PNAS,* 94:13287–13291 (1991).

*Primary Examiner*—Deborah Crouch
(74) *Attorney, Agent, or Firm*—Townsend and Townsend and Crew LLP

(57) ABSTRACT

The invention includes identification of specific markers, the elevation of which in central nervous tissue is associated with Alzheimer's Disease. The invention also includes improved assay methods for selecting compounds useful in reducing or preventing onset of the pathology associated with Alzheimer's Disease.

43 Claims, 6 Drawing Sheets

Homozygous perfused hippocampus

Closed= Transgenic
Open = Non transgenic

Closed=Transgenic homozygote
Open + Non transgenic

Figure 6A

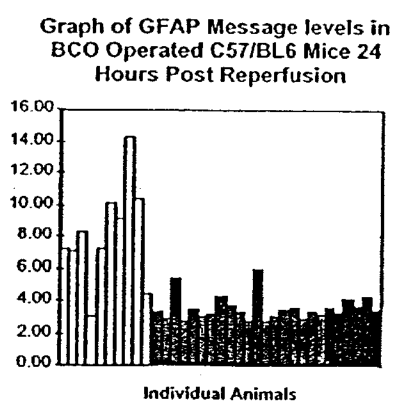

Figure 6B

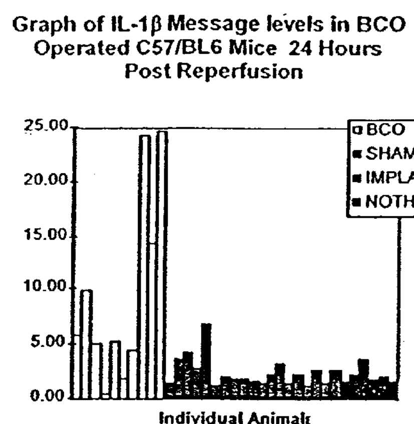

Figure 6C

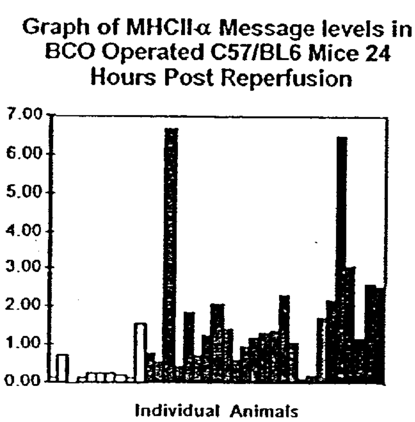

Figure 6D

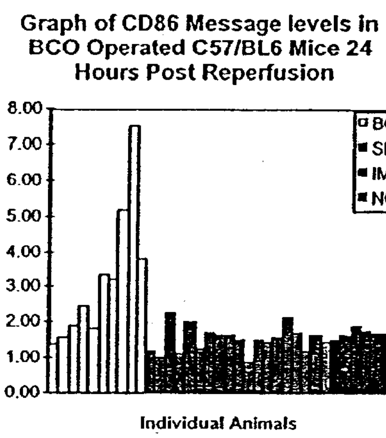

Inflammatory markers were evaluated in four groups of animals. BCO: animals receiving a 15 minute period of occlusion of blood flow, in addition to transmitter implant, are shown in white as the first group, n= 10. Sham: animals receiving transmitter implant, and BCO surgery without occlusion of blood flow, are shown in dark gray as the second group, n=10. Implant: animals receiving a transmitter implant are shown in light gray as the third group, n = 9. Nothing: animals receiving no manipulation are shown in black, as the fourth group, n = 6.

SEQUENCE LISTING

```
<160> NUMBER OF SEQ ID NOS: 85

<210> SEQ ID NO 1
<211> LENGTH: 20
<212> TYPE: DNA
<213> ORGANISM: Artificial Sequence
<220> FEATURE:
<223> OTHER INFORMATION: MoGapdh251F forward primer

<400> SEQUENCE: 1

gggaagccca tcaccatctt                                                   20


<210> SEQ ID NO 2
<211> LENGTH: 20
<212> TYPE: DNA
<213> ORGANISM: Artificial Sequence
<220> FEATURE:
<223> OTHER INFORMATION: MoGapdh363R reverse primer

<400> SEQUENCE: 2

gccttctcca tggtggtgaa                                                   20


<210> SEQ ID NO 3
<211> LENGTH: 29
<212> TYPE: DNA
<213> ORGANISM: Artificial Sequence
<220> FEATURE:
<223> OTHER INFORMATION: MoGapdh272T probe

<400> SEQUENCE: 3

caggagcgag accccactaa catcaaatg                                         29


<210> SEQ ID NO 4
<211> LENGTH: 20
<212> TYPE: DNA
<213> ORGANISM: Artificial Sequence
<220> FEATURE:
<223> OTHER INFORMATION: mGFAP-420F forward primer

<400> SEQUENCE: 4

ctggaggtgg agagggacaa                                                   20


<210> SEQ ID NO 5
<211> LENGTH: 22
<212> TYPE: DNA
<213> ORGANISM: Artificial Sequence
<220> FEATURE:
<223> OTHER INFORMATION: mGFAP-489R reverse primer

<400> SEQUENCE: 5

tggtttcatc ttggagcttc tg                                                22


<210> SEQ ID NO 6
<211> LENGTH: 21
<212> TYPE: DNA
<213> ORGANISM: Artificial Sequence
<220> FEATURE:
<223> OTHER INFORMATION: mGFAP-443T probe

<400> SEQUENCE: 6

tgcacaggac ctcggcaccc t                                                 21
```

<210> SEQ ID NO 7
<211> LENGTH: 22
<212> TYPE: DNA
<213> ORGANISM: Artificial Sequence
<220> FEATURE:
<223> OTHER INFORMATION: mMip1a128F forward primer

<400> SEQUENCE: 7
caagtcttct cagcgccata tg 22

<210> SEQ ID NO 8
<211> LENGTH: 27
<212> TYPE: DNA
<213> ORGANISM: Artificial Sequence
<220> FEATURE:
<223> OTHER INFORMATION: mMip1a229F reverse primer

<400> SEQUENCE: 8
ggtttcaaaa tagtcaacga tgaattg 27

<210> SEQ ID NO 9
<211> LENGTH: 29
<212> TYPE: DNA
<213> ORGANISM: Artificial Sequence
<220> FEATURE:
<223> OTHER INFORMATION: mMip1a172T probe

<400> SEQUENCE: 9
ctgcttctcc tacagccgga agattccac 29

<210> SEQ ID NO 10
<211> LENGTH: 20
<212> TYPE: DNA
<213> ORGANISM: Artificial Sequence
<220> FEATURE:
<223> OTHER INFORMATION: mTNFa-420F forward primer

<400> SEQUENCE: 10
ctggaggtgg agagggacaa 20

<210> SEQ ID NO 11
<211> LENGTH: 22
<212> TYPE: DNA
<213> ORGANISM: Artificial Sequence
<220> FEATURE:
<223> OTHER INFORMATION: mTNFa-492R reverse primer

<400> SEQUENCE: 11
ggttggtttc atcttggagc tt 22

<210> SEQ ID NO 12
<211> LENGTH: 21
<212> TYPE: DNA
<213> ORGANISM: Artificial Sequence
<220> FEATURE:
<223> OTHER INFORMATION: mTNFa-442T probe

<400> SEQUENCE: 12
ttgcacagga cctcggcacc c 21

<210> SEQ ID NO 13
<211> LENGTH: 21
<212> TYPE: DNA
<213> ORGANISM: Artificial Sequence
<220> FEATURE:

<223> OTHER INFORMATION: mIL1B-2F forward primer

<400> SEQUENCE: 13
gcagggttcg aggcctaata g 21

<210> SEQ ID NO 14
<211> LENGTH: 23
<212> TYPE: DNA
<213> ORGANISM: Artificial Sequence
<220> FEATURE:
<223> OTHER INFORMATION: mIL1B-114R reverse primer

<400> SEQUENCE: 14
gtggcatttc acagttgagt tca 23

<210> SEQ ID NO 15
<211> LENGTH: 25
<212> TYPE: DNA
<213> ORGANISM: Artificial Sequence
<220> FEATURE:
<223> OTHER INFORMATION: mIL1B-30T probe

<400> SEQUENCE: 15
tgggatcctc tccagccaag cttcc 25

<210> SEQ ID NO 16
<211> LENGTH: 16
<212> TYPE: DNA
<213> ORGANISM: Artificial Sequence
<220> FEATURE:
<223> OTHER INFORMATION: mCD86 #2-250F forward primer

<400> SEQUENCE: 16
ggccgcacga gctttg 16

<210> SEQ ID NO 17
<211> LENGTH: 20
<212> TYPE: DNA
<213> ORGANISM: Artificial Sequence
<220> FEATURE:
<223> OTHER INFORMATION: mCD86 #2-321R reverse primer

<400> SEQUENCE: 17
cgagcccatg tccttgatct 20

<210> SEQ ID NO 18
<211> LENGTH: 32
<212> TYPE: DNA
<213> ORGANISM: Artificial Sequence
<220> FEATURE:
<223> OTHER INFORMATION: mCD86 #2-267T probe

<400> SEQUENCE: 18
caggaacaac tggactctac gacttcacaa tg 32

<210> SEQ ID NO 19
<211> LENGTH: 14
<212> TYPE: DNA
<213> ORGANISM: Artificial Sequence
<220> FEATURE:
<223> OTHER INFORMATION: mMHC II(Ia), Li chain-418F forward primer

<400> SEQUENCE: 19
cgcgggcgcc ataa 14

-continued

```
<210> SEQ ID NO 20
<211> LENGTH: 21
<212> TYPE: DNA
<213> ORGANISM: Artificial Sequence
<220> FEATURE:
<223> OTHER INFORMATION: mMHC II(Ia), Li chain-479R reverse primer

<400> SEQUENCE: 20

actcccaggc cagaagatag g                                                21


<210> SEQ ID NO 21
<211> LENGTH: 25
<212> TYPE: DNA
<213> ORGANISM: Artificial Sequence
<220> FEATURE:
<223> OTHER INFORMATION: mMHC II(Ia), Li chain-433TR probe

<400> SEQUENCE: 21

cttccatgtc cagtggctca ctgca                                            25


<210> SEQ ID NO 22
<211> LENGTH: 20
<212> TYPE: DNA
<213> ORGANISM: Artificial Sequence
<220> FEATURE:
<223> OTHER INFORMATION: mMHC II(Ia), a chain-294F forward primer

<400> SEQUENCE: 22

ccaccccagc taccaatgag                                                  20


<210> SEQ ID NO 23
<211> LENGTH: 22
<212> TYPE: DNA
<213> ORGANISM: Artificial Sequence
<220> FEATURE:
<223> OTHER INFORMATION: mMHC II(Ia), a chain-386R reverse primer

<400> SEQUENCE: 23

ccacaaagca gatgagggtg tt                                               22


<210> SEQ ID NO 24
<211> LENGTH: 22
<212> TYPE: DNA
<213> ORGANISM: Artificial Sequence
<220> FEATURE:
<223> OTHER INFORMATION: mMHC II(Ia), a chain-335T probe

<400> SEQUENCE: 24

cccaagtccc ctgtgctgct gg                                               22


<210> SEQ ID NO 25
<211> LENGTH: 24
<212> TYPE: DNA
<213> ORGANISM: Artificial Sequence
<220> FEATURE:
<223> OTHER INFORMATION: R.GAPDH-750F forward primer

<400> SEQUENCE: 25

tgccaagtat gatgacatca agaa                                             24


<210> SEQ ID NO 26
<211> LENGTH: 20
<212> TYPE: DNA
<213> ORGANISM: Artificial Sequence
<220> FEATURE:
<223> OTHER INFORMATION: R.GAPDH-820R reverse primer
```

<400> SEQUENCE: 26
agcccaggat gcccttttagt 20

<210> SEQ ID NO 27
<211> LENGTH: 18
<212> TYPE: DNA
<213> ORGANISM: Artificial Sequence
<220> FEATURE:
<223> OTHER INFORMATION: R.GAPDH-781T probe

<400> SEQUENCE: 27
aagcaggcgg ccgagggc 18

<210> SEQ ID NO 28
<211> LENGTH: 22
<212> TYPE: DNA
<213> ORGANISM: Artificial Sequence
<220> FEATURE:
<223> OTHER INFORMATION: R.GFAP-2099F forward primer

<400> SEQUENCE: 28
ctcaatgacc gctttgctag ct 22

<210> SEQ ID NO 29
<211> LENGTH: 18
<212> TYPE: DNA
<213> ORGANISM: Artificial Sequence
<220> FEATURE:
<223> OTHER INFORMATION: R.GFAP-2165R reverse primer

<400> SEQUENCE: 29
ccagcgcctt gttttgct 18

<210> SEQ ID NO 30
<211> LENGTH: 24
<212> TYPE: DNA
<213> ORGANISM: Artificial Sequence
<220> FEATURE:
<223> OTHER INFORMATION: R.GFAP-2122T probe

<400> SEQUENCE: 30
catcgagaag gtccgcttcc tgga 24

<210> SEQ ID NO 31
<211> LENGTH: 21
<212> TYPE: DNA
<213> ORGANISM: Artificial Sequence
<220> FEATURE:
<223> OTHER INFORMATION: R.MHC II a-196F forward primer

<400> SEQUENCE: 31
ggcacagtca aggctgagaa t 21

<210> SEQ ID NO 32
<211> LENGTH: 18
<212> TYPE: DNA
<213> ORGANISM: Artificial Sequence
<220> FEATURE:
<223> OTHER INFORMATION: R.MHC II a-266R reverse primer

<400> SEQUENCE: 32
tcgcgctcct ggaagatg 18

<210> SEQ ID NO 33
<211> LENGTH: 27

-continued

<212> TYPE: DNA
<213> ORGANISM: Artificial Sequence
<220> FEATURE:
<223> OTHER INFORMATION: R.MHC II a-220T probe

<400> SEQUENCE: 33
aagctggtca tcaatgggaa acccatc 27

<210> SEQ ID NO 34
<211> LENGTH: 21
<212> TYPE: DNA
<213> ORGANISM: Artificial Sequence
<220> FEATURE:
<223> OTHER INFORMATION: Osteopontin forward primer

<400> SEQUENCE: 34
gatttgcttt tgcctgtttg g 21

<210> SEQ ID NO 35
<211> LENGTH: 22
<212> TYPE: DNA
<213> ORGANISM: Artificial Sequence
<220> FEATURE:
<223> OTHER INFORMATION: Osteopontin reverse primer

<400> SEQUENCE: 35
tgagctgcca gaatcagtca ct 22

<210> SEQ ID NO 36
<211> LENGTH: 21
<212> TYPE: DNA
<213> ORGANISM: Artificial Sequence
<220> FEATURE:
<223> OTHER INFORMATION: Osteopontin probe

<400> SEQUENCE: 36
ttgcctcctc cctcccggtg a 21

<210> SEQ ID NO 37
<211> LENGTH: 21
<212> TYPE: DNA
<213> ORGANISM: Artificial Sequence
<220> FEATURE:
<223> OTHER INFORMATION: VitD3-24OHase forward primer

<400> SEQUENCE: 37
cccaagtgtg ccattcacaa c 21

<210> SEQ ID NO 38
<211> LENGTH: 22
<212> TYPE: DNA
<213> ORGANISM: Artificial Sequence
<220> FEATURE:
<223> OTHER INFORMATION: VitD3-24OHase reverse primer

<400> SEQUENCE: 38
tcctttgggt agcgtgtatt ca 22

<210> SEQ ID NO 39
<211> LENGTH: 23
<212> TYPE: DNA
<213> ORGANISM: Artificial Sequence
<220> FEATURE:
<223> OTHER INFORMATION: VitD3-24OHase probe

<400> SEQUENCE: 39

-continued cggacccttg acaagccaac cgt 23

<210> SEQ ID NO 40
<211> LENGTH: 19
<212> TYPE: DNA
<213> ORGANISM: Artificial Sequence
<220> FEATURE:
<223> OTHER INFORMATION: MCP-1 forward primer

<400> SEQUENCE: 40
gctggagcat ccacgtgtt 19

<210> SEQ ID NO 41
<211> LENGTH: 23
<212> TYPE: DNA
<213> ORGANISM: Artificial Sequence
<220> FEATURE:
<223> OTHER INFORMATION: MCP-1 reverse primer

<400> SEQUENCE: 41
gcctactcat tgggatcatc ttg 23

<210> SEQ ID NO 42
<211> LENGTH: 25
<212> TYPE: DNA
<213> ORGANISM: Artificial Sequence
<220> FEATURE:
<223> OTHER INFORMATION: MCP-1 probe

<400> SEQUENCE: 42
agccagatgc agttaacgcc ccact 25

<210> SEQ ID NO 43
<211> LENGTH: 21
<212> TYPE: DNA
<213> ORGANISM: Artificial Sequence
<220> FEATURE:
<223> OTHER INFORMATION: IL-10 forward primer

<400> SEQUENCE: 43
agagaagcat ggcccagaaa t 21

<210> SEQ ID NO 44
<211> LENGTH: 19
<212> TYPE: DNA
<213> ORGANISM: Artificial Sequence
<220> FEATURE:
<223> OTHER INFORMATION: IL-10 reverse primer

<400> SEQUENCE: 44
cgcatcctga gggtcttca 19

<210> SEQ ID NO 45
<211> LENGTH: 29
<212> TYPE: DNA
<213> ORGANISM: Artificial Sequence
<220> FEATURE:
<223> OTHER INFORMATION: IL-10 probe

<400> SEQUENCE: 45
cttctcaccc agggaattca aatgctcct 29

<210> SEQ ID NO 46
<211> LENGTH: 22
<212> TYPE: DNA
<213> ORGANISM: Artificial Sequence -continued
<220> FEATURE:
<223> OTHER INFORMATION: IL-12 p40, #1 forward primer

<400> SEQUENCE: 46
acagcaccag cttcttcatc ag 22

<210> SEQ ID NO 47
<211> LENGTH: 23
<212> TYPE: DNA
<213> ORGANISM: Artificial Sequence
<220> FEATURE:
<223> OTHER INFORMATION: IL-12 p40, #1 reverse primer

<400> SEQUENCE: 47
ttcaaaggct tcatctgcaa gtt 23

<210> SEQ ID NO 48
<211> LENGTH: 24
<212> TYPE: DNA
<213> ORGANISM: Artificial Sequence
<220> FEATURE:
<223> OTHER INFORMATION: IL-12 p40, #1 probe

<400> SEQUENCE: 48
catcatcaaa ccagacccgc ccaa 24

<210> SEQ ID NO 49
<211> LENGTH: 22
<212> TYPE: DNA
<213> ORGANISM: Artificial Sequence
<220> FEATURE:
<223> OTHER INFORMATION: IL-12 p40 #2 forward primer

<400> SEQUENCE: 49
acatctaccg aagtccaatg ca 22

<210> SEQ ID NO 50
<211> LENGTH: 25
<212> TYPE: DNA
<213> ORGANISM: Artificial Sequence
<220> FEATURE:
<223> OTHER INFORMATION: IL-12 p40 #2 reverse primer

<400> SEQUENCE: 50
catgaggaat tgtaatagcg atcct 25

<210> SEQ ID NO 51
<211> LENGTH: 21
<212> TYPE: DNA
<213> ORGANISM: Artificial Sequence
<220> FEATURE:
<223> OTHER INFORMATION: IL-12 p40 #2 probe

<400> SEQUENCE: 51
aggcgggaat gtctgcgtgc a 21

<210> SEQ ID NO 52
<211> LENGTH: 19
<212> TYPE: DNA
<213> ORGANISM: Artificial Sequence
<220> FEATURE:
<223> OTHER INFORMATION: INF-gamma, #1 forward primer

<400> SEQUENCE: 52
cagcaacagc aaggcgaaa 19

<210> SEQ ID NO 53
<211> LENGTH: 21
<212> TYPE: DNA
<213> ORGANISM: Artificial Sequence
<220> FEATURE:
<223> OTHER INFORMATION: INF-gamma, #1 reverse primer

<400> SEQUENCE: 53
ctggacctgt gggttgttga c 21

<210> SEQ ID NO 54
<211> LENGTH: 31
<212> TYPE: DNA
<213> ORGANISM: Artificial Sequence
<220> FEATURE:
<223> OTHER INFORMATION: INF-gamma, #1 probe

<400> SEQUENCE: 54
aggatgcatt catgagtatt gccaagtttg a 31

<210> SEQ ID NO 55
<211> LENGTH: 23
<212> TYPE: DNA
<213> ORGANISM: Artificial Sequence
<220> FEATURE:
<223> OTHER INFORMATION: INF-gamma, #2 forward primer

<400> SEQUENCE: 55
acaatgaacg ctacacactg cat 23

<210> SEQ ID NO 56
<211> LENGTH: 20
<212> TYPE: DNA
<213> ORGANISM: Artificial Sequence
<220> FEATURE:
<223> OTHER INFORMATION: INF-gamma, #2 reverse primer

<400> SEQUENCE: 56
cgtggcagta acagccagaa 20

<210> SEQ ID NO 57
<211> LENGTH: 25
<212> TYPE: DNA
<213> ORGANISM: Artificial Sequence
<220> FEATURE:
<223> OTHER INFORMATION: INF-gamma, #2 probe

<400> SEQUENCE: 57
ttggctttgc agctcttcct catgg 25

<210> SEQ ID NO 58
<211> LENGTH: 23
<212> TYPE: DNA
<213> ORGANISM: Artificial Sequence
<220> FEATURE:
<223> OTHER INFORMATION: CD3 epsilon forward primer

<400> SEQUENCE: 58
gagttgacgt gccctctaga cag 23

<210> SEQ ID NO 59
<211> LENGTH: 22
<212> TYPE: DNA
<213> ORGANISM: Artificial Sequence
<220> FEATURE:
<223> OTHER INFORMATION: CD3 epsilon reverse primer -continued

<400> SEQUENCE: 59
tatcatgctt ctgaggcagc tc 22

<210> SEQ ID NO 60
<211> LENGTH: 31
<212> TYPE: DNA
<213> ORGANISM: Artificial Sequence
<220> FEATURE:
<223> OTHER INFORMATION: CD3 epsilon probe

<400> SEQUENCE: 60
tggccatttt tttcccattt taagttctcg t 31

<210> SEQ ID NO 61
<211> LENGTH: 21
<212> TYPE: DNA
<213> ORGANISM: Artificial Sequence
<220> FEATURE:
<223> OTHER INFORMATION: CD4, #1 forward primer

<400> SEQUENCE: 61
aggtggagtt gtgggtgttc a 21

<210> SEQ ID NO 62
<211> LENGTH: 18
<212> TYPE: DNA
<213> ORGANISM: Artificial Sequence
<220> FEATURE:
<223> OTHER INFORMATION: CD4, #1 reverse primer

<400> SEQUENCE: 62
caggctctgc ccttgcaa 18

<210> SEQ ID NO 63
<211> LENGTH: 26
<212> TYPE: DNA
<213> ORGANISM: Artificial Sequence
<220> FEATURE:
<223> OTHER INFORMATION: CD4, #1 probe

<400> SEQUENCE: 63
agtgaccttc agtccgggta ccagcc 26

<210> SEQ ID NO 64
<211> LENGTH: 23
<212> TYPE: DNA
<213> ORGANISM: Artificial Sequence
<220> FEATURE:
<223> OTHER INFORMATION: CD4, #2 forward primer

<400> SEQUENCE: 64
aggaaagagg aggtggagtt gtg 23

<210> SEQ ID NO 65
<211> LENGTH: 18
<212> TYPE: DNA
<213> ORGANISM: Artificial Sequence
<220> FEATURE:
<223> OTHER INFORMATION: CD4, #2 reverse primer

<400> SEQUENCE: 65
caggctctgc ccttgcaa 18

<210> SEQ ID NO 66

<211> LENGTH: 29
<212> TYPE: DNA
<213> ORGANISM: Artificial Sequence
<220> FEATURE:
<223> OTHER INFORMATION: CD4, #2 probe

<400> SEQUENCE: 66
tgttcaaagt gaccttcagt ccgggtacc 29

<210> SEQ ID NO 67
<211> LENGTH: 20
<212> TYPE: DNA
<213> ORGANISM: Artificial Sequence
<220> FEATURE:
<223> OTHER INFORMATION: IgG-1 forward primer

<400> SEQUENCE: 67
tggaggtgca cacagctcag 20

<210> SEQ ID NO 68
<211> LENGTH: 20
<212> TYPE: DNA
<213> ORGANISM: Artificial Sequence
<220> FEATURE:
<223> OTHER INFORMATION: IgG-1 reverse primer

<400> SEQUENCE: 68
tgagcggaaa gtgctgttga 20

<210> SEQ ID NO 69
<211> LENGTH: 20
<212> TYPE: DNA
<213> ORGANISM: Artificial Sequence
<220> FEATURE:
<223> OTHER INFORMATION: IgG-1 probe

<400> SEQUENCE: 69
ctgctcctcc cggggttgcg 20

<210> SEQ ID NO 70
<211> LENGTH: 19
<212> TYPE: DNA
<213> ORGANISM: Artificial Sequence
<220> FEATURE:
<223> OTHER INFORMATION: IgK (light chain) forward primer

<400> SEQUENCE: 70
ggcgtcctga acagttgga 19

<210> SEQ ID NO 71
<211> LENGTH: 19
<212> TYPE: DNA
<213> ORGANISM: Artificial Sequence
<220> FEATURE:
<223> OTHER INFORMATION: IgK (light chain) reverse primer

<400> SEQUENCE: 71
cgtgagggtg ctgctcatg 19

<210> SEQ ID NO 72
<211> LENGTH: 29
<212> TYPE: DNA
<213> ORGANISM: Artificial Sequence
<220> FEATURE:
<223> OTHER INFORMATION: IgK (light chain) probe

<400> SEQUENCE: 72

-continued

```
tgatcaggac agcaaagaca gcacctaca                                       29


<210> SEQ ID NO 73
<211> LENGTH: 67
<212> TYPE: DNA
<213> ORGANISM: Artificial Sequence
<220> FEATURE:
<223> OTHER INFORMATION: Osteopontin marker

<400> SEQUENCE: 73

gatttgcttt tgcctgtttg gcattgcctc ctccctcccg gtgaaagtga ctgattctgg     60
cagctca                                                               67


<210> SEQ ID NO 74
<211> LENGTH: 73
<212> TYPE: DNA
<213> ORGANISM: Artificial Sequence
<220> FEATURE:
<223> OTHER INFORMATION: VitD3-24OHase marker

<400> SEQUENCE: 74

cccaagtgtg ccattcacaa ctcggaccct tgacaagcca accgttctgg gtgaatacac     60
gctacccaaa gga                                                        73


<210> SEQ ID NO 75
<211> LENGTH: 96
<212> TYPE: DNA
<213> ORGANISM: Artificial Sequence
<220> FEATURE:
<223> OTHER INFORMATION: MCP-1 marker

<400> SEQUENCE: 75

gctggagcat ccacgtgttg gctcagccag atgcagttaa cgccccactc acctgctgct     60
actcattcac cagcaagatg atcccaatga gtaggc                               96


<210> SEQ ID NO 76
<211> LENGTH: 72
<212> TYPE: DNA
<213> ORGANISM: Artificial Sequence
<220> FEATURE:
<223> OTHER INFORMATION: IL-10 marker

<400> SEQUENCE: 76

agagaagcat ggcccagaaa tcaaggagca tttgaattcc ctgggtgaga agctgaagac     60
cctcaggatg cg                                                         72


<210> SEQ ID NO 77
<211> LENGTH: 73
<212> TYPE: DNA
<213> ORGANISM: Artificial Sequence
<220> FEATURE:
<223> OTHER INFORMATION: IL-12 p40, #1 marker

<400> SEQUENCE: 77

acagcaccag cttcttcatc agggacatca tcaaaccaga cccgcccaag aacttgcaga     60
tgaagccttt gaa                                                        73


<210> SEQ ID NO 78
<211> LENGTH: 74
<212> TYPE: DNA
<213> ORGANISM: Artificial Sequence
<220> FEATURE:
<223> OTHER INFORMATION: IL-12 p40, #2 marker

<400> SEQUENCE: 78

acatctaccg aagtccaatg caaaggcggg aatgtctgcg tgcaagctca ggatcgctat     60
```

-continued

```
tacaattcct catg                                                    74


<210> SEQ ID NO 79
<211> LENGTH: 73
<212> TYPE: DNA
<213> ORGANISM: Artificial Sequence
<220> FEATURE:
<223> OTHER INFORMATION: IFN-gamma, #1 marker

<400> SEQUENCE: 79

cagcaacagc aaggcgaaaa aggatgcatt catgagtatt gccaagtttg aggtcaacaa    60
cccacaggtc cag                                                       73


<210> SEQ ID NO 80
<211> LENGTH: 73
<212> TYPE: DNA
<213> ORGANISM: Artificial Sequence
<220> FEATURE:
<223> OTHER INFORMATION: IFN-gamma, #2 marker

<400> SEQUENCE: 80

acaatgaacg ctacacactg catcttggct ttgcagctct tcctcatggc tgtttctggc    60
tgttactgcc acg                                                       73


<210> SEQ ID NO 81
<211> LENGTH: 79
<212> TYPE: DNA
<213> ORGANISM: Artificial Sequence
<220> FEATURE:
<223> OTHER INFORMATION: CD3 epsilon marker

<400> SEQUENCE: 81

gagttgacgt gccctctaga cagtgacgag aacttaaaat gggaaaaaaa tggccaagag    60
ctgcctcaga agcatgata                                                 79


<210> SEQ ID NO 82
<211> LENGTH: 50
<212> TYPE: DNA
<213> ORGANISM: Artificial Sequence
<220> FEATURE:
<223> OTHER INFORMATION: CD4, #1 marker

<400> SEQUENCE: 82

aggtggagtt gtgggtgttc aaagtgacct tcagtccggg taccagcctg              50


<210> SEQ ID NO 83
<211> LENGTH: 78
<212> TYPE: DNA
<213> ORGANISM: Artificial Sequence
<220> FEATURE:
<223> OTHER INFORMATION: CD4, #2 marker

<400> SEQUENCE: 83

aggaaagagg aggtggagtt gtgggtgttc aaagtgacct tcagtccggg taccagcctg    60
ttgcaagggc agagcctg                                                  78


<210> SEQ ID NO 84
<211> LENGTH: 62
<212> TYPE: DNA
<213> ORGANISM: Artificial Sequence
<220> FEATURE:
<223> OTHER INFORMATION: IgG-1 marker

<400> SEQUENCE: 84

tggaggtgca cacagctcag acgcaacccc gggaggagca gttcaacagc actttccgct    60
ca                                                                   62
```

-continued

```
<210> SEQ ID NO 85
<211> LENGTH: 69
<212> TYPE: DNA
<213> ORGANISM: Artificial Sequence
<220> FEATURE:
<223> OTHER INFORMATION: IgK (light chain) marker

<400> SEQUENCE: 85

ggcgtcctga acagttggac tgatcaggac agcaaagaca gcacctacag catgagcagc     60
accctcacg                                                             69
```

SELECTING COMPOUNDS TO REDUCE INFLAMMATION ASSOCIATED WITH ALZHEIMER'S DISEASE

CROSS-REFERENCE TO RELATED APPLICATIONS

This application claims the benefit of U.S. patent application Ser. No. 60/193,847, filed Mar. 30, 2000, which is incorporated by reference herein in its entirety.

FIELD OF THE INVENTION

The invention relates to screening markers and assays useful in testing for therapeutics to treat neurodegenerative disorders, particularly certain neurodegenerative diseases having an inflammatory component, such as Alzheimer's Disease (AD).

BACKGROUND OF THE INVENTION

Progressive neurodegeneration of the central nervous system is characteristic of a number of debilitating diseases, including Alzheimer's Disease. In its progressive stages, Alzheimer's Disease (AD) is characterized by the presence of amyloid plaques and neurofibrillatory tangles in the brain, neuronal degeneration, inflammatory responses, vascular damage and dementia (Hardy and Higgins (1992) *Science* 256: 184).

Transgenic animals, such as the PDAPP mouse can be used both to study the progression of the disease as well as to test compounds and/or intervention strategies directed at retarding progression of the disease (e.g., U.S. Pat. No. 5,811,633). However, the number of compounds that can be readily tested in such animal models has been limited to some degree by their dependence on histological analysis; hence, it may be impractical to use such models for high volume or high throughput screening of potential therapeutic compounds.

Recently, the term "Alzheimer's Disease-like inflammation" has been applied to a pathology that is characterized by the presence of amyloid plaques composed of amyloid β-peptide (a 40–42 amino acid fragment of the β-amyloid precursor protein (APP)), astrocytosis and microgliosis. Various types of plaques have been characterized including neuritic plaques, which are associated with cognitive decline in AD. Neuritic plaques are associated with abnormal dystrophic neurites and inflammatory responses including activated microglia and astrocytes. In addition, while a number of cytokines have been reported to be elevated in AD, there has been no definitive etiological correlation between elevation of specific marker proteins and development of the disease state. That is, although a number of inflammatory cytokines have been reported to be elevated in the brains and CSF of Alzheimer's patients, it has not been clear whether such cytokines are contributory or incidental to the disease process. However, retrospective studies suggest that use of anti-inflammatory drugs is associated with delayed onset of AD.

It is the discovery of the present invention that the appearance of certain protein or polynucleotide markers, including certain inflammatory cell-related markers and cytokines, described herein, is coincident with the onset of morphohistological correlates of Alzheimer's Disease in a standard experimental model of the disease, a transgenic mouse which carries a mutant form of APP, for example, the PDAPP mouse. This discovery enables the development of faster, more quantitative drug screening assays for therapeutics for prevention or treatment of AD. Related to this discovery is the finding, also described herein, that the same markers are elevated in response to certain insults to nervous tissue. This finding forms the basis for new, simpler and faster animal models for Alzheimer's Disease and more particularly, for in vivo screening assays for drugs effective in preventing or reducing the symptoms of AD.

These and other objects and features of the invention will become more fully apparent when the following detailed description of the invention is read in conjunction with the accompanying drawings.

BRIEF DESCRIPTION OF THE FIGURES

FIGS. 6A–6D levels of mRNA for GFAP (6A) IL1β (6B) MHC IIα (6C) and CD86 (6D) in individual BCO-operated mice (n=10), sham-operated mice (n=9), radiotransmitter-implanted mice (n=9) and untreated mice (n=6) 24 hours post reperfusion, where BCO-operated mice are indicated by open bars.

DETAILED DESCRIPTION OF THE INVENTION

I. Definitions

Figure 1A:
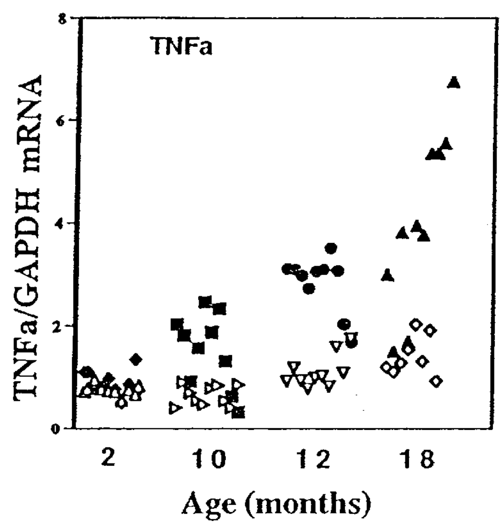
FIGS. 1A–1D show levels of mRNA for TNFα (1A), MIP1α (1B), GFAP (1C) and IL1β (1C) measured in transgenic (closed symbols) and control (open symbols) mice at 2, 10, 12 and 18 months of age, where mRNA levels are normalized to GAPDH levels.
Figure 1B:
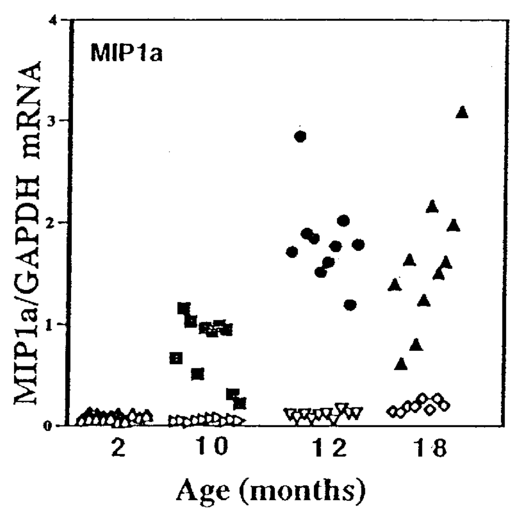
Figure 1C:
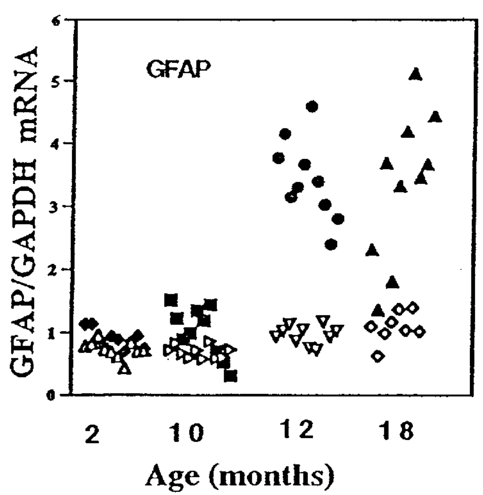
Figure 1D:
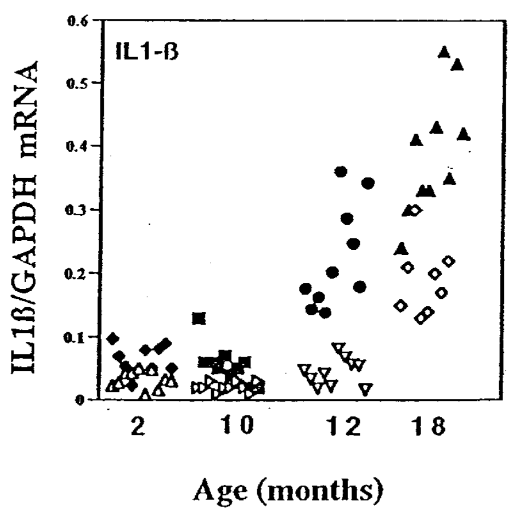

Unless otherwise indicated, all terms used herein have the same meanings as they would to one skilled in the art of the present invention.

As used herein, the term "marker" refers to any detectable biological correlate of a neurodegenerative disease characterized by AD-like inflammation, particularly Alzheimer's Disease. Preferred markers are protein markers which can be measured by detection of the protein, any specific antigenic site on the protein, a coding sequence specific to the protein, such as messenger RNA (mRNA) or cDNA derived from such mRNA. Exemplary methods for detecting and measuring markers are provided in the Examples.

The term "Alzheimer's Disease", abbreviated herein as "AD" refers to a neurodegenerative disease of the central nervous system characterized by amyloid plaques and neurofibrillatory tangles concentrated in certain vulnerable regions of the brain such as the hippocampus and cortex. Various types of plaques are found in AD, including, but not limited to neuritic plaques associated with abnormal dystrophic neurites. Also characteristic of the disease is the presence of an inflammatory response in the CNS, including activated microglia and astrocytes.

The term "IL1β" refers to a member of the interleukin family of macrophage-derived cytokines. The IL1β polypeptide is known to be a stimulator of inflammatory responses in the periphery. As used herein, the term may refer to the polypeptide or its specific DNA or RNA coding sequence, which polypeptide or coding sequence may be derived from any biological source or tissue.

The term "TNFα" refers to Tumor Necrosis Factor α, a macrophage-derived cytokine that is also known as a mediator of inflammation in the periphery. As used herein, the term may refer to the polypeptide or its specific DNA or RNA coding sequence, which polypeptide or coding sequence may be derived from any biological source or tissue.

The term "MIP1α" refers to Macrophage Inflammatory Protein α, a macrophage derived chemokine which is chemotatic for monocytes, eosinophils, basophils and lymphocytes. As used herein, the term may refer to the polypeptide or its specific DNA or RNA coding sequence, which polypeptide or coding sequence may be derived from any biological source or tissue.

The term "GFAP" refers to Glial Fibrillar Associated Protein, an astrocyte-associated protein which is associated with activation of astrocytes in response to wounding, inflammation or neuronal damage. As used herein, the term may refer to the polypeptide or its specific DNA or RNA coding sequence, which polypeptide or coding sequence may be derived from any biological source or tissue.

The term "CD86" refers to an antigen which is present on activated cells of the monocyte lineage and which is involved in presentation of antigen during activation of T-lymphocytes.

The term "MHC II" refers to Major Histocompatibility Complex II, a protein antigen which is present on activated microglia and is involved in presentation of antigens to T-lymphocytes. "MHC IIα" refers to the alpha chain of the complex.

The term "MHC II Li" refers to the invariant chain of MHC II, which is co-regulated with MHC II.

The term "fractalkine" refers to a member of the CX3C family of chemokines which contains both a chemokine and a mucin domain.

The term "CX3CR1" refers to a receptor for fractalkine, which has been localized to T-lymphocytes, natural killer (NK) cells, and macrophages.

II. AD Markers

The present invention is based on the discovery that certain marker proteins and/or their specific coding sequences are induced in a manner that correlates in time with the appearance of morphological symptoms of Alzheimer's Disease (AD) in transgenic mice that carry the gene for a mutated form of APP. These mice, which include but are not limited to PDAPP mice as disclosed in U.S. Pat. No. 5,811,633, incorporated herein by reference, display prominent AD pathology, and provide an animal model of AD. Such transgenic mice represent the first animal model of AD that displays the same type of chronic, low level and local CNS inflammation that is characteristic of AD. By about 12 months of age, these mice begin to exhibit CNS AD-associated inflammatory pathology in hippocampus and cortex, brain regions which also display prominent AD pathology. This pathology, which includes AD-type amyloid plaques, neurofibrillatory tangles and activated microglia and astrocytes, progresses over time.

More specifically, it is the discovery of the present invention that specific marker proteins are detectable by non-histological means in PDAPP mice as well as in other, newly recognized models of AD inflammation, as described herein. That is, CD86, MHC IIα and MHC II Li, previously identified as microglia-specific markers, appear in 12-month old homozygous PDAPP mice. In addition, the cytokine markers IL-1β, MIP-1α, and TNFα and the astrocyte-specific marker GFAP are also induced in homozygous PDAPP mice in a manner that parallels appearance of activated microglia and astrocytes and amyloid plaques in mice.

Certain markers, which may be the same as, a subset of, or different than the markers referred to above, are indicative of the efficacy of a given drug or treatment regimen in reducing plaque burden. These markers, referred to herein as "efficacy markers" are also identified by the methods disclosed herein. Examples of such efficacy markers are provided.

Part A of this section describes the identities and forms of the various AD markers which form the basis of the present invention. Part B provides guidance for methods of detecting such markers. Section II describes additional animal models suitable for measuring the appearance of such AD-specific markers and discloses the utility of such models for more rapid screening of compounds for treatment of Alzheimer's Disease.

A. Identification of AD-specific Markers

Co-pending, co-owned U.S. patent application U.S. Ser. No. 09/149,718 filed Sep. 8, 1998, incorporated herein by reference, describes a number of proteins involved in neuroinflammatory responses which can serve as markers for AD-like inflammation. Experiments carried out in support of the present invention demonstrate the correlation between the appearance or induction of certain of these markers and onset of Alzheimer's Disease symptomology in the PDAPP mouse. More specifically, these include several cytokine-related messages (IL-1β, MIP1α, TNFα), an astrocyte specific marker (GFAP), as well as activated monocyte-associated antigen CD86 and activated microglia-associated antigens MHC IIα and MHC II Li.

As described in more detail in Part IIB, in experiments carried out in support of the present invention, AD markers were detected using quantitative PCR methods that allow for detection of "rare" mRNAs encoding the markers. Exemplary assay conditions and primer/probe sequences specific for each of the foregoing markers are provided in Example 1 and summarized in Tables 2 and 3 therein. It is understood that such assays are provided by way of example only and are not meant to limit the scope of the invention; any method capable of detecting any form of the marker, such as the protein, including antigenic portion(s) thereof, or any form of coding sequence (e.g., mRNA, cDNA, DNA) thereof, may be used in carrying out the methods of the invention. However, preferred methods of detection will include those methods capable of detecting relatively low quantities of the marker with a degree of accuracy that allows comparison and differentiation among samples. Preferably, such methods will provide quantitative data for comparison test and control samples.

In further support of the invention, expression of markers TNFα, MIP1α GFAP and IL1β was measured in tissues derived from homozygous PDAPP mice at 2, 10, 12 and 18 months of age by RT-PCR (reverse transcription polymerase chain reaction; e.g., White, B. A., Ed., *PCR Cloning Protocols,* Humana Press, Totoua, N.J., 1997) analysis of mRNA derived from hippocampal brain tissue, as described in Example 1. In these studies, sample values were normalized with reference to internal GDAPH (glyceraldehyde-3-phosphate dehydrogenase). Results from these experiments are shown in FIGS. 1A–1D. As shown, induction of expression of the markers in the transgenic animal follows the time-course of inflammation established by histological analysis of brain samples from the mice. GFAP and IL1-β were demonstrated to be induced between 10 and 12 months of age, around the time that activated astrocytes appear, according to histological evaluation. TNFα and MIP1α were induced somewhat earlier, at 10 months. These results correlate the appearance of these markers to the ongoing plaque associated inflammation measured by conventional histological methods, such as those described in co-owned, co-pending U.S. patent application U.S. Ser. No. 09/149,718, incorporated herein by reference. Osteopontin is also elevated in PDAPP mice compared to non-transgenic mice (see Example 5).

Figure 2A:
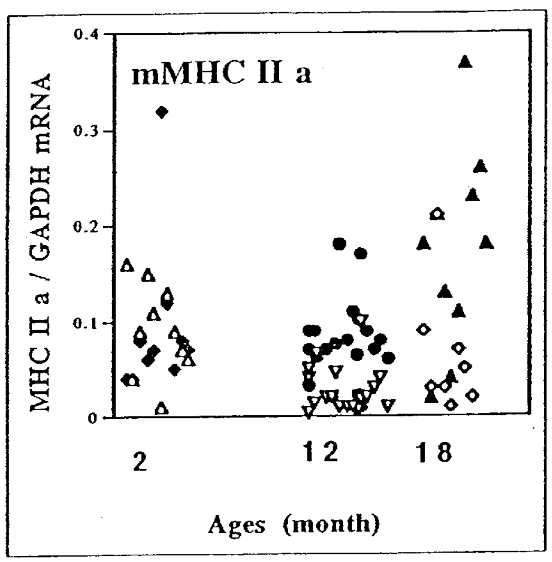
FIGS. 2A–2C show levels of mRNA for MHC IIα (2A), CD86 (2B), and MHC II Li (2C) measured in transgenic (closed symbols) and control (open symbols) mice at 2, 12, and 18 months of age, where mRNA levels are normalized to GAPDH mRNA levels.
Figure 2B:
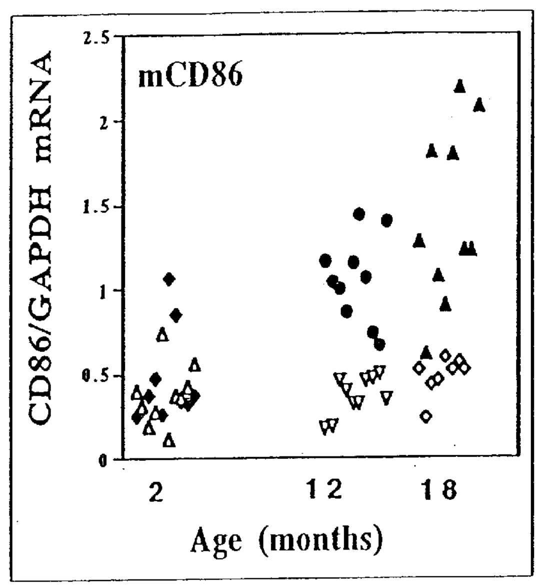
Figure 2C:
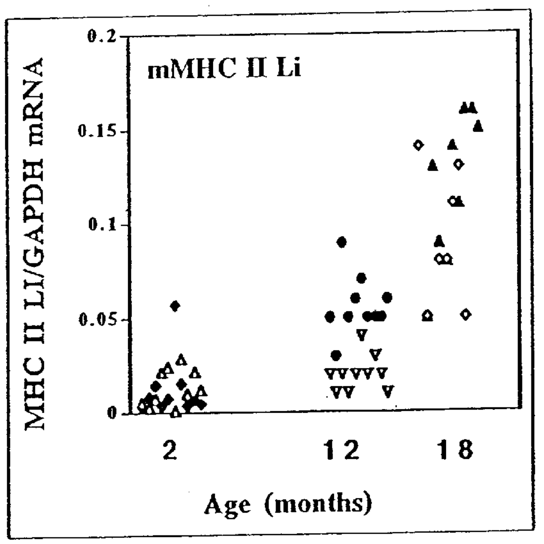

Quantitative PCR assays were also developed for three microglia specific markers (murine MHC IIα chain, MHC II Li chain and CD86). Assay conditions and primer/probes are shown in Tables 2 and 3 in Example 1. As illustrated, markers MHC IIα and CD86 were significantly elevated in the hippocampus of 12 and 18 month old homozygous PDAPP mice compared to non-transgenic control animals (FIGS. 2A and 2B), while MHC II Li was significantly elevated in 12 month old homozygous PDAPP mice as compared to control animals (FIG. 2C). These data are summarized in Table 1, below. The use of the quantitative PCR assays, or other similar assays, has the advantage over previously used histochemical analysis that it can be adapted to high thoroughput screening assays, such as QT-PCR, for rapid and analysis of multiple samples in a manner that is much less labor-intensive.

TABLE 1

| | | 2 month | 12 month | 18 month |
|---|---|---|---|---|
| MHC IIa | NTg | 0.090 | 0.028 | 0.064 |
| | Tg | 0.091 | 0.078 | 0.175 |
| MHCII Li | NTg | 0.014 | 0.020 | 0.112 |
| | Tg | 0.013 | 0.055 | 0.130 |
| CD86 | NTg | 0.379 | 0.368 | 0.484 |
| | Tg | 0.461 | 1.054 | 1.419 |

The foregoing studies validate the use of the various inflammatory markers of the invention in chronicling the onset of AD pathology. Additional studies are described in Examples 4 and 5. As discussed in Section II, below, these markers can be used as efficacy indicators in screening assays for compounds for use in reducing, eliminating or inhibiting development of AD.

B. Quantitative Assays for Detecting AD-specific Markers

Marker proteins or their coding sequences can be detected according to any of a number of methods known in the art, including but not limited to detection of protein antigens using antigen specific antibodies in conjunction with appropriate reporter systems, detection of coding regions using specific hybridization probes, and the like. Particularly preferred methods include quantitative PCR, such as RT-PCR, which detects and permits analysis of mRNA transcripts present in brain tissue. Exemplary quantitative PCR methods are described in Example 1.

Briefly, RNA was extracted from tissue samples according to standard methods known in the art, such as using a S.N.A.P.® RNA extraction kit (Invitrogen, Carlsbad, Calif.). Marker analysis was carried out by PCR, using a Perkin Elmer ABI Prism 7700 Sequence Detection System. (Perkin Elmer, Foster City, Calif.). PCR reactions were set up according to standard methods known in the art. More specifically, forward and reverse primers were selected based on the known RNA coding sequences for the various markers. Exemplary primers are described in Table 2. Detailed methods are found in Example 1. Other quantitative methods of detection can be used to determine the concentration of specific marker present in a particular tissue sample. For example, where concentrations of marker are high enough to be detectable by protein localization techniques, the concentration of expressed protein can be measured directly, such as using antibodies directed to the marker in standard immunoassay techniques.

III. In vivo Assay Systems

According to an important feature of the invention, markers described and validated as described above are particularly useful in the context of animal models of Alzheimer's Disease. Currently, the potential in vivo screening of compounds for efficacy in the treatment of AD-type inflammation is limited to studies conducted in the PDAPP mouse and measurement of morphohistological correlates of AD, such as plaque burden, neuritic dystrophy, immunohistochemical detected activated microglia and astrocytes. Such methods may not be optimal for high throughput drug screening, since they are labor intensive and since it takes the PDAPP mouse about 12 months to develop AD-type inflammatory pathology, and the availability of PDAPP mice is often limited.

Therefore, it is also desirable to have a more rapid animal model of CNS. Criteria for such models include the following: First, the majority of inflammatory markers identified as altered in the transgenic (PDAPP) mouse should also be altered in the surrogate model. Second, the inflammation should be localized to a site within the CNS, ideally to regions of the brain that are vulnerable in AD, such as the hippocampus or cortex. Third, the model should have a significant time advantage over the PDAPP mouse for screening compounds.

Experiments carried out in support of the present invention have revealed that many of the above-described markers for AD are elevated in two short-term animal models: the Bilateral Common Carotid Occlusion (BCO) model of global ischemia (mouse) and the Rat Facial Nerve Axotomy (RFNA) model of neurodegeneration. Both these models produce localized neuronal damage and inflammatory responses over a relatively short period of time. Accordingly, both of these models can be used as a surrogate for the transgenic mouse model known in the art and described, for example in co-pending U.S. patent application U.S. Ser. No. 09/149,718, incorporated herein by reference.

A. Bilateral Common Carotid Occlusion (BCO) Model of Global Ischemia

Models of global ischemia which produce a transient arrest of cerebral blood flow are generally utilized to evaluate neuronal loss and inflammatory responses due to cerebral ischemia (stroke) or myocardial infarction. Thus neuronal loss, as evaluated by histopathology, is first localized to hippocampal sectors CA1 and CA3, followed by damage to the neocortex. C57BL/6 mice exhibit enhanced susceptibility to global cerebral ischemic injury because they possess a poorly defined posterior communicating artery (Fujii et al., 1997). In addition, ischemic damage in this model manifests itself as a drop in body temperature and rise in gross motor activity during the first twenty hours post reperfusion (Mileson, et al., 1991, Gerhardt, et al., 1988). Thus, the end points of body temperature and gross motor activity can be used to evaluate the induction of the ischemia.

In experiments carries out in support of the present invention, detailed in Example 2, the time course and change in mRNA expression levels were measured in the hippocampus for some of the markers of the present invention after induction of global ischemia in C57BL/6 mice. Measurements of body temperature and gross motor activity were taken and evaluated for the individual animals. The data shown herein were obtained 24 or 48 hours post-ischemia.

a. Telemetry Measurements

Figure 3:
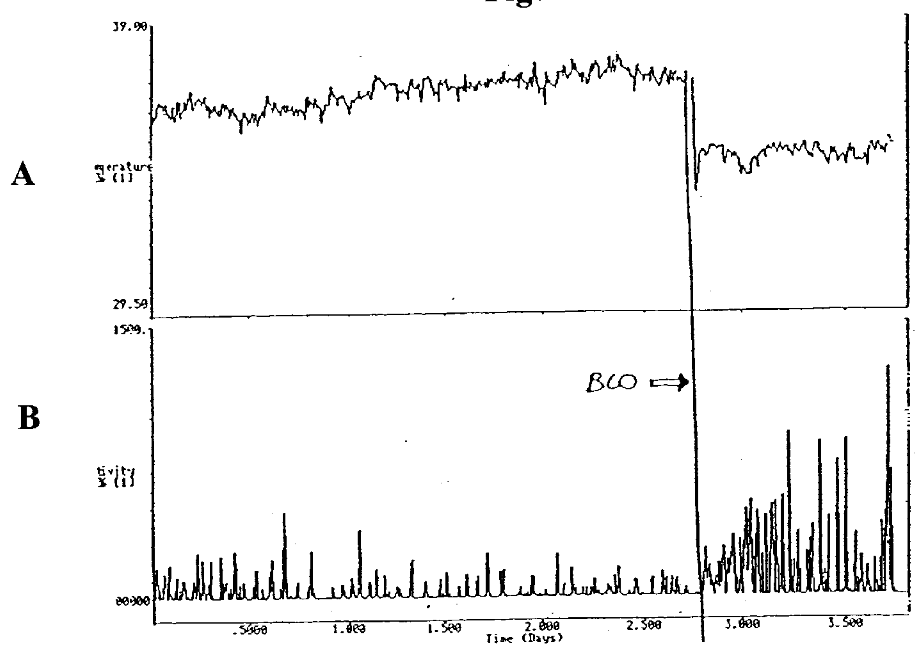
FIGS. 3A and 3B show a time course tracing of rat body temperatures before and after bilateral carotid occlusion (BCO), as indicated, in a rat where temperature readings (° C.) were taken every five minutes (3A), and gross motor activity tracing based on activity readings measured in units/5 minues (3B)
Figure 4:
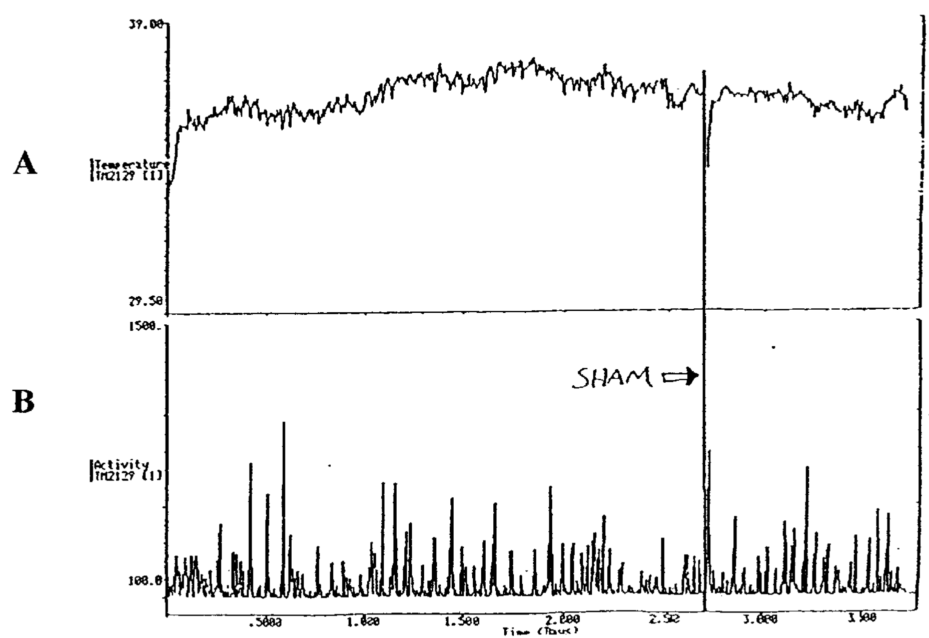
FIGS. 4A and 4B a time course tracing of rat body temperatures before and after sham operation for BCO, as indicated, in a rat where temperature readings of (°C.) were taken every five minutes (4A), and gross motor activity tracing based on activity readings measured in units/5 minutes (4B)

Body temperature and gross motor activity were used as indicators of ischemic damage. These two parameters were measured via a radiotransmitter implanted in the test mouse abdomen two days prior to the BCO procedure. Once baseline measurements were obtained, another surgical procedure was performed to isolate the common carotid arteries. A clip was placed on each of the arteries for 15 minutes, while body temperature was maintained at 37° C. This surgically induced, controlled occlusion of blood flow while maintaining a body temperature of 37° C. is what is associated with consistent reproducible global ischemia. At the end of the occlusion period, the clips were removed and the carotid arteries were visually inspected to confirm that blood flow had been re-established. The mouse was returned to its cage for continuous monitoring of body temperature and motor activity following the ischemic episode. Typical body temperature and gross motor activity readouts are shown below for data collected from individual BCO and sham animals (FIGS. 3 and 4). The decrease in body temperature and increase in gross motor activity in the BCO operated animal were noticeably different to those in the sham animal.

b. Quantitative PCR Measurements

Figure 5A:
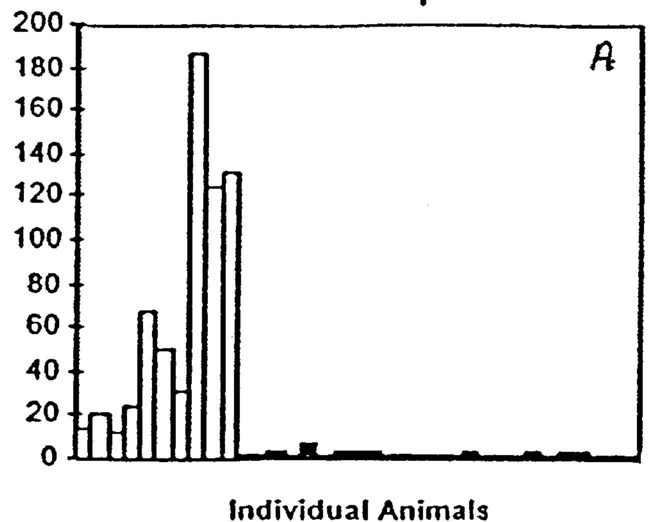
FIGS. 5A and 5B show levels of mRNA for MIP1α (5A) and TNFα (5B) in BCO-operated mice (n=10), sham-operated mice (n=9), radiotransmitter-implanted mice (n=9) and untreated mice (n=6) 24 hours post reperfusion, where BCO-operated mice are indicated by open bars.
Figure 5B:
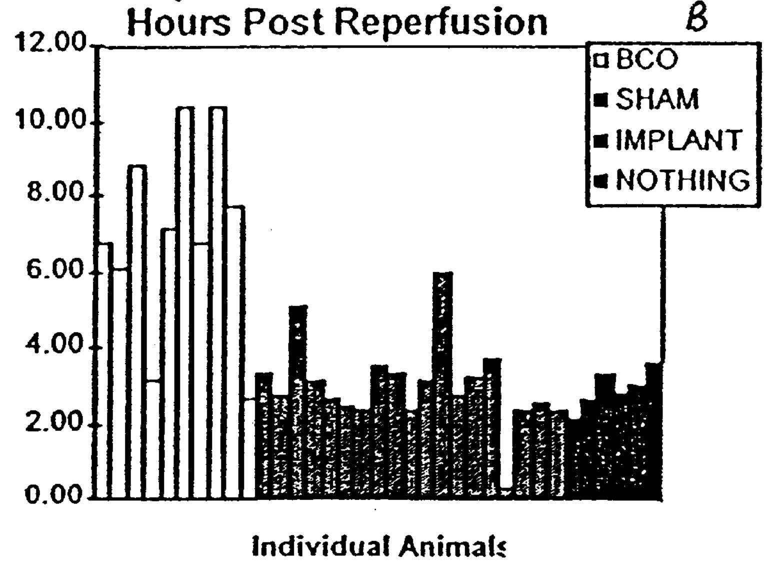

After a defined period of reperfusion, the animals were euthanized, perfused with 0.9% saline and the hippocampi from both hemispheres were removed. RNA was extracted from the tissue samples and quantitative PCR used to evaluate message levels of RNAs encoding inflammatory markers. Quantitative PCR was conducted according to the protocols detailed in Example 1 and described in Section I, above. As shown in FIGS. 5 and 6, a subset of inflammatory markers, previously identified as elevated in the PDAPP mouse, were also elevated in the hippocampus 24 hours after global ischemia.

The BCO model of global ischemia has satisfied many of the criteria set forth for a model of AD-type inflammation. As shown in FIGS. 5(A,B) and 6(A–D), many of the AD markers described herein were up-regulated within 24 hours after induction of ischemia. Thus the target of the inflammatory response in BCO includes a site within the CNS, the hippocampus. Furthermore, 24 hours after BCO, all the markers that are up-regulated in the PDAPP mouse, are also up-regulated in BCO, with the exception of one marker, MHC II.

B. Rat Facial Nerve Axotomy Model

Axotomy (transection) of the peripheral facial nerve in experimental models results in degeneration and ultimate regeneration of motoneurons in cranial nerve VII. This model was tested and validated as a relatively quick and reproducible means for inducing CNS inflammation, as evidenced by the induction of some of the inflammatory markers described in Section II, above. As discussed below, the two markers tested in this model (GFAP and MHC II Iα) were shown to be elevated in the denervated region (side contralateral to lesion).

Methods for performing the axotomy procedure, isolating facial nuclei and extracting RNA for quantitative analysis are described in Example 3.

Figure 7A:
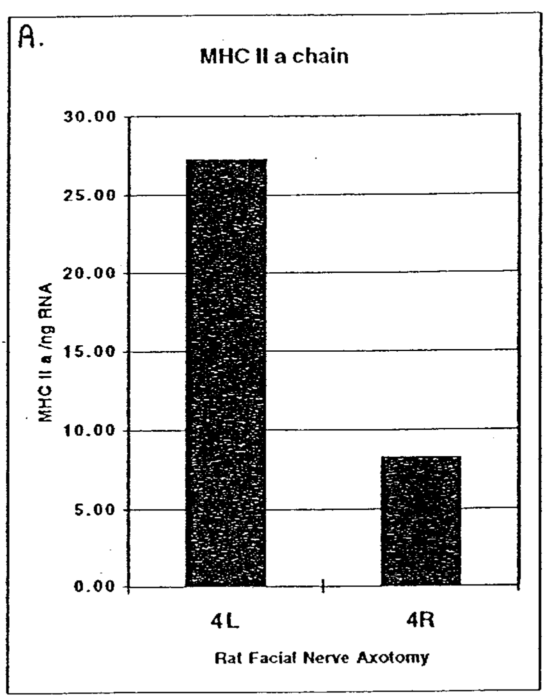
FIGS. 7A and 7B show induction of MHC II (7A) and GFAP (7B) on the left (4L) denervated side compared to the control right (4R) side after rat facial nerve axotomy (RFNA) where tissues from four animals were pooled for each analysis.
Figure 7B:
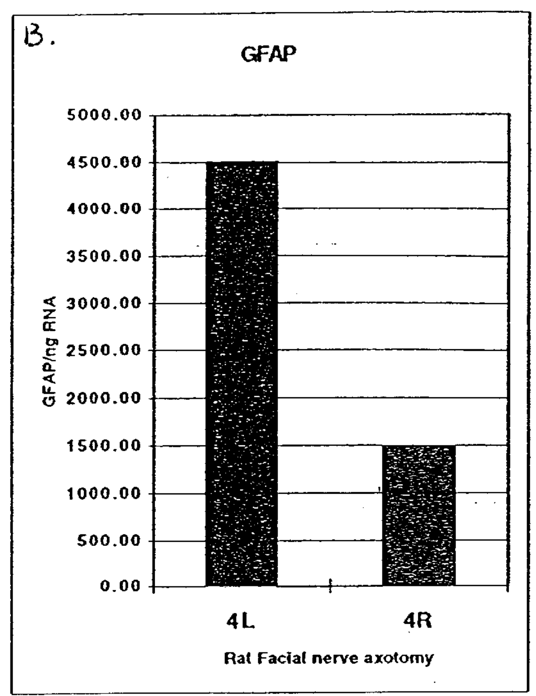

Quantitative PCR assays were developed for two rat inflammatory markers (rat MHC IIα and rat GFAP), and control rat GAPDH. Assay conditions and primer/probes are shown in Tables 1 and 2. From these studies it was found that rat spleen polyA+RNA could be used as a standard for MHC II a chain, and total RNA extracted from a rat mixed brain culture as standard for GFAP. Using these RNA standards, relative expression levels of MHC II, and GFAP transcripts were measured in facial nuclei ipsilateral to the lesion (4L), as well as in the contralateral control nuclei (4R). The levels of the control RNA marker, GAPDH, did not change when normalized to total RNA so that marker data can be either normalized to total RNA or to GAPDH. FIGS. 7A and 7B show that MHC IIα and GFAP mRNAs, normalized to total RNA, are elevated in the ipsilateral facial nucleus nerve axotomy model. These data were obtained from RNA extracted from pooled nuclei dissected from 4 rats. Hence, the data represents an average difference among 4 animals.

IV. Utility

Markers of the present invention can be used in conjunction with a number of assay formats designed to evaluate the efficacy of candidate compounds for potential therapeutic use in Alzheimer's Disease. Guidance for setting up and evaluating such assays is found with reference to the description and working examples described herein. More specifically, the invention includes use of the described markers to monitor the efficacy of compounds tested in various animal or cellular models of Alzheimer's Disease. Based on the disclosures of the present invention, persons skilled in the art will be able to set up an appropriate in vitro or in vivo assay system and monitor the system for induction of the various markers described herein (e.g., IL1β, TNFα, MIP-1α, GFAP, MHC IIα, CD86, fractalkine, CX3CR1) as well as other markers found to be associated with AD-like inflammation, such as markers described in co-pending, co-owned U.S. patent application U.S. Ser. No. 09/149,718, incorporated herein by reference.

Described herein are two exemplary animal models that illustrate the versatility of the present invention. These systems, previously used for assessing the effects of various forms of acute neuronal insult, now find utility in the practice of the present invention in the context of providing a relatively short-term assay for screening compounds having the potential for treating Alzheimer's Disease and related chronic neurodegenerative diseases characterized by AD-like inflammation.

Using the mouse bilateral carotid artery occlusion (BCO) model by way of example, depending upon the particular drug administration paradigm determined by the investigator, a test compound is administered to test animal either before or after the occlusion period. The animal is subjected to BCO, then given time to recover as described. The animal is then sacrificed (for example 24 or 48 hours or longer following occlusion), critical brain regions isolated and processed for marker detection. While as few as one marker determination may be made, it is preferred that at least two or more markers be measured. In accordance with the six specific markers exemplified herein, a significant reduction in the induced levels of such markers, compared to the induced levels observed in control animals, is indicative of drug efficacy in the model.

By way of example, mice are divided into control (BCO surgery) and test (test drug+BCO surgery) groups. Additional mice may be sham-operated (prepared and incisions made for surgery, including isolation of carotid arteries from surrounding tissue) and unoperated for additional controls. Test compounds are administered to selected animals, according to a pre-determined paradigm that takes into consideration the number of animals needed in each group in order to make meaningful (statistically significant) comparasions. Such administering can be carried out by any of a number of modes well known in the art, including but not limited to intravenous, intraventricular, intrathecal, epidural, intramuscular, nasal insufflation, and the like. Preferred methods of administration will be those that provide consistently high levels of test compound to the affected brain regions, particularly the cortex and hippocampus. For example, compound may be administered intra-arterially to the carotid arteries just prior to or following ligation; alternatively, compound may be infused intraventricularly before, during and/or after ligation of the carotid arteries, in order to assess the therapeutic window of opportunity.

Markers will be measured in tissues taken from the test animal subjects, especially brain cortical and hippocampal tissues. Comparison between groups will be carried out, using standard statistical means of evaluation known in the art. A compound will be deemed of therapeutic potential, if it reduces the amount of induction relative to control values of one or more of the markers described above. That is, control ligated animals will be expected to show an increase (induction) of one or more of the markers. In contrast, successfully treated animals will be expected to show lower values, more in line with those observed with non-operated controls.

Following drug screening, it is understood that candidate compounds will require further testing, for example, for toxicity, prior to regulatory approval and control.

Also described herein is identification, using PDAPP mice, of "efficacy markers." Table 4 lists a number of molecules, some of which (e.g., CD86) overlap with the markers described above, which have been shown to be modulated during plaque clearance in PDAPP mice. That is, in experiments carried out in support of the present invention, the brains of control and AN1792 drug-treated PDAPP mice were examined at age 17 months for plaque levels and levels of a variety of candidate markers, using the techniques described herein. Levels of the molecules listed in Table 4 were found to be significantly elevated in treated mice and to correlate with plaque clearance. Such efficacy markers are particularly useful in drug screening using afflicted mice, such as PDAPP mice, or other animal models of neurodegeneration or amyloidosis, including Alzheimer's disease. Such biochemical markers greatly reduce the time needed for processing samples, compared to standard histological techniques, as well as reduce the amount of brain sample needed for analysis. Various immunological formats (e.g., ELISA, RIA), as well as PCR-based assays can be devised to provide the efficacy information for drug screening. Such biochemical analysis also provides a foundation for setting up high throughput screening assays, according to methods known in the art.

In addition, the methods described herein are readily adapted to diagnostic assay development. For example, many of the markers described are found on peripheral cells, as well as in the brain tissue samples described herein. The markers described herein are tested for modulation in a test peripheral tissue (such as a lymphocyte) and, if modulated in a manner that correlates with the observed modulation in brain studies, may serve as surrogate markers in the drug screening studies (in test animals) or in drug efficacy studies (in animals or in human clinical trials).

The following examples illustrate, but in no way are intended to limit the present invention.

Materials and Methods

EXAMPLE 1

Quantitative PCR

A. Isolation of RNA

RNA was isolated from brain tissues using the S.N.A.P.™ Total RNA Isolation Kit (Invitrogen, Carlsbad, Calif.) according to manufacturer's instructions, with the following modifications: the tissue was homogenized for 20 seconds using a rotor-stator homogenizer (Fisher Scientific). The DNA digestion step was repeated a second time following isopropanol precipitation.

B. Quantitative RT-PCR

Quantitative PCR assays were run on a Perkin Elmer 7700 Sequencer using methods and materials provided by Perkin Elmer (Applied Biosystems Division, Foster City, Calif.). Primers and fluorescent probes were obtained from Perkin Elmer; the sequences and concentrations of primers and probes used for the various assays are listed in Table 1 below. PCR reactions were set up using approximately 300 nM concentrations of each of the forward and reverse primers, 100 nM probe and RNA extracted from the tissue of interest (20 ng). Each reaction also included a standard RNA for comparison. Data were normalized to total RNA or to GAPDH. Standard curves were run using standard RNA prepared from the appropriate tissue (e.g., brain total RNA). Sample results were normalized to the amount of RNA measured by OD and or control message (e.g., GAPDH).

TABLE 2 assay conditions
inflammatory markers

| assay | primer F. | primer R | probe | UNKN RNA | STND RNA | DILUTION |
|---|---|---|---|---|---|---|
| rMHC II a | 300 nM | 300 nM | 100 nM | 20 ng/well | Spleen RNA 4 ng/well | ⅓ |
| rGFAP | 300 nM | 300 nM | 100 nM | 2 ng/well | MBC RNA 16 ng/well | ⅓ |
| rGAPDH | 300 nM | 300 nM | 100 nM | 2 ng/well | MBC RNA 20 ng/well | ⅓ |
| mGAPDH | 200 nM | 200 nM | 100 nM | 20 ng/well | mouse brain (ctx + hip) 40 ng/well | ⅓ |
| mMHC II Li | 900 nM | 900 nM | 100 nM | 20 ng/well | " | ⅓ |
| mMHC II a | 300 nM | 300 nM | 100 nM | 20 ng/well | " | ⅓ |
| mCD86 | 300 nM | 300 nM | 100 nM | 20 ng/well | " | ⅓ |
| mMIP1a | 300 nM | 300 nM | 100 nM | 20 ng/well | " | ⅓ |
| mIL1 | 300 nM | 300 nM | 100 nM | 20 ng/well | " | ⅓ |
| mGFAP | 300 nM | 300 nM | 100 nM | 20 ng/well | " | ⅓ |
| mTNFa | 300 nM | 300 nM | 100 nM | 20 ng/well | " | ⅓ |

TABLE 3 qtPCR primers and probes, inflammatory efficacy markers

| assay | Genbank # | forward primer | | reverse primer | |
|---|---|---|---|---|---|
| murine GAPDH | | Name: | MoGapdh251F | Name: | MoGapdh363R |
| | | Sequence: | GGGAAGCCCATCACCATCTT (SEQ ID NO:1) | Sequence: | GCCTTCTCCATGGTGGTGAA (SEQ ID NO:2) |
| murine GFAP | | Name: | mGFAP-420F | Name: | mGFAP-489R |
| | | Sequence: | CTGGAGGTGGAGAGGGACAA (SEQ ID NO:4) | Sequence: | TGGTTTCATCTTGGAGCTTCTG (SEQ ID NO:5) |
| murine MIP1α | | Name: | mMip1a128F | Name: | mMip1a229R |
| | | Sequence: | CAAGTCTTCTCAGCGCCATATG (SEQ ID NO:7) | Sequence: | GGTTTCAAAATAGTCAACGATGAATTG (SEQ ID NO:8) |
| murine TNF-α | | Name: | mTNFa-420F | Name: | mTNFa-492R |
| | | Sequence: | CTGGAGGTGGAGAGGGACAA (SEQ ID NO:10) | Sequence: | GGTTGGTTTCATCTTGGAGCTT (SEQ ID NO:11) |
| murine Il1-β | | Name: | mIL1B-2F | Name: | mIL1B-114R |
| | | Sequence: | GCAGGGTTCGAGGCCTAATAG (SEQ ID NO:13) | Sequence: | GTGGCATTTCACAGTTGAGTTCA (SEQ ID NO:14) |
| murine CD86 | | Name: | mCD86 #2-250F | Name: | mCD86 #2-321R |
| | | Sequence: | GGCCGCACGAGCTTTG (SEQ ID NO:16) | Sequence: | CGAGCCCATGTCCTTGATCT (SEQ ID NO:17) |
| murine MHCII Ii | | Name: | mMHC II(Ia), Li chain-418F | Name: | mMHC II(Ia), Ii chain-479R |
| | | Sequence: | CGCGGGCGCCATAA (SEQ ID NO:19) | Sequence: | ACTCCCAGGCCAGAAGATAGG (SEQ ID NO:20) |
| murine MHCIIα | | Name: | mMHC II(Ia), a chain-294F | Name: | mMHC II(Ia), a chain-386R |
| | | Sequence: | CCACCCCAGCTACCAATGAG (SEQ ID NO:22) | Sequence: | CCACAAAGCAGATGAGGGTGTT (SEQ ID NO:23) |
| rat GAPDH | M17701 | Name: | R GAPDH-750F | Name: | R.GAPDH-820R |
| | | Sequence: | TGCCAAGTATGATGACATCAAGAA (SEQ ID NO:25) | Sequence: | AGCCCAGGATGCCCTTTAGT (SEQ ID NO:26) |
| rat GFAP | z48978 | Name: | R GFAP-2099F | Name: | R GFAP-2165R |
| | | Sequence: | CTCAATGACCGCTTTGCTAGCT (SEQ ID NO:28) | Sequence: | CCAGCGCCTTGTTTTGCT (SEQ ID NO:29) |
| rat MHCII α | M29311 | Name: | R MHC II a-196F | Name: | R MHC II a-266R |
| | | Sequence: | GGCACAGTCAAGGCTGAGAAT (SEQ ID NO:31) | Sequence: | TCGCGCTCCTGGAAGATG (SEQ ID NO:22) |

| assay | Genbank # | probe | |
|---|---|---|---|
| murine GAPDH | | Name: | MoGapdh272T |
| | | Sequence: | CAGGAGCGAGACCCCACTAACATCAAATG (SEQ ID NO:3) |
| murine GFAP | | Name: | mGFAP-443T |
| | | Sequence: | TGCACAGGACCTCGGCACCCT (SEQ ID NO:6) |
| murine MIP1α | | Name: | mMiP1a172T |
| | | Sequence: | CTGCTTCTCCTACAGCCGGAAGATTCCAC (SEQ ID NO:9) |
| murine TNF-α | | Name: | mTNFa-442T |
| | | Sequence: | TTGCACAGGACCTCGGCACCC (SEQ ID NO:12) |
| murine Il1-β | | Name: | mIL1B-30T |
| | | Sequence: | TGGGATCCTCTCCAGCCAAGCTTCC (SEQ ID NO:15) |
| murine CD86 | | Name: | mCD86 #2-267T |
| | | Sequence: | CAGGAACAACTGGACTCTACGACTTCACAATG (SEQ ID NO:18) |
| murine MHCII Ii | | Name: | mMHC II(Ia), Ii chain-433TR |
| | | Sequence: | CTTCCATGTCCAGTGGCTCACTGCA (SEQ ID NO:21) |
| murine MHCIIα | | Name: | mMHC II(Ia), a chain-335T |
| | | Sequence: | CCCAAGTCCCCTGTGCTGCTGG (SEQ ID NO:24) |
| rat GAPDH | M17701 | Name: | R GAPDH-781T |
| | | Sequence: | AAGCAGGCGGCCGAGGGC (SEQ ID NO:27) |
| rat GFAP | z48978 | Name: | R GFAP-2122T |
| | | Sequence: | CATCGAGAAGGTCCGCTTCCTGGA (SEQ ID NO:30) |
| rat MHCII α | M29311 | Name: | R MHC II a-220T |
| | | Sequence: | AAGCTGGTCATCAATGGGAAACCCATC (SEQ ID NO:33) |

TABLE 4

| Efficacy Markers |
| --- |
| Mac-1 |
| MHC II α chain |
| MHC II (Ia) Li chain |
| CD86 |
| MCP-1 |
| CCR5 |
| CCR2 |
| GRO(= KC) |
| MIP2 |
| IL-10 |
| IL-12 p40 |
| IFN-γ |
| CD3 ε |
| CD4 |
| IgG-1 |
| K (light chain) |
| GFAP |

EXAMPLE 2

Bilateral Common Carotid Occlusion (BC) in Mice

A. Transmitter Implantation

At least 2 days before induction of global ischemia mice were anesthetized with 1.5–3.0% isoflurane carried in 100% oxygen in a holding chamber until they were unconscious. Mice were transferred to a thermoregulated heating pad to maintain body temperature at 37° C. Mice were given continuous gas anesthesia by a nose cone apparatus, and the percentage of isoflurane adjusted within the pre-determined range (1.5–3.0%) until the animal reached a surgical plane of anesthesia as monitored by lack of pedal (toe pinch) reflex. The abdominal surface was shaved to remove hair and scrubbed with Betadine® (povidone, an anti-microbial solution) to ensure an aseptic area. All instruments utilized for the surgical procedure were sterilized daily by soaking in cetylcide for 30 minutes, rinsed in sterile water and air dried. For subsequent surgeries instruments were sterilized by heated glass bead sterilization or soaking as previously described.

A ventral midline incision was made (approximately 2 cm in length) along the midline of the abdomen through the skin and abdominal muscle wall, and a sterile radio transmitter (3 g, 1.4 $cm^3$) was placed inside the abdomen. The muscle layer was closed with absorbable 4-0 vicryl suture using a pattern of interrupted sutures. The skin was closed with a 4-0 or 5-0 monofilament nylon suture coated with tissue adhesive, using a pattern of interrupted sutures. Gas anesthesia was withdrawn and the mice were left on the heating pad and observed by the surgeon continuously until they regained consiousness and could maintain a ventral posture. The mice were returned to their cages on receiving pads.

B. Bilateral Occlusion of the Common Carotid Arteries

As described for implantation of the radio transmitters, mice were anesthetized to reach the surgical plane of anesthesia. All instruments were maintained for sterility as described above. The mice were placed on thermoregulated heating pads and their body temperature maintained between 36.0 and 37.5° C. throughout the procedure. The throat was shaved and gently scrubbed with Betadine®. An incision (0.5–1.0 cm) perpendicular to midline was made through the skin just superior to the sternum. The common carotid arteries were visually identified; it was not necessary to cut musculature to gain access. The carotid arteries were blunt dissected from surrounding tissue, vein and vagus nerve, and a thread of 3.0 silk suture was passed underneath each artery. The thread was used to lift the artery away from the surrounding tissue and a small arterial clip was placed around the artery to provide occlusion. The clip was allowed to remain in place for 15 minutes, during which time the mouse was continually anesthetized, and body temperature was noted at 5 minute intervals. The clips were removed and the carotid arteries were visually inspected to confirm blood flow. The silk sutures were removed and the skin was closed with a series of interrupted stitches using 4-0 or 5-0 monofilament nylon suture. The mouse was returned to its cage, and the cage placed back on the receiving pad.

At a specified time after the BCO surgery, the mice were anesthetized with sodium pentobarbital (0.25 ml administered intraperitoneally of 32 mg/ml) and monitored until there is a lack of pedal reflex. The animals were transcardially perfused with ice cold, sterile saline. The brain was removed, and the hippocampus was dissected out and snap frozen on dry ice in 'RNase free tubes'. RNA was then extracted from these samples and quantitative PCR is run according to methods set forth in Example 1.

EXAMPLE 3

Rat Facial Nerve Axotomy

Two month old male Wistar rats weighing 280–300 gm were subjected to a unilateral transection of the facial nerve 2–3 mm distal to the stylomastoid formen under isoflurane anesthesia. Seven days later, animals were euthanized. Facial nuclei from lesioned (left, n=4) and control (right, n=4) sides were microdissected with a coronal brain matrix (A 1.4–3.3 mm) and a puncher (V 0–1.8 mm, L 0.9–1.7 mm). Frozen 20 μm sections were taken and were cresyl stained to insure that the entire facial nucleus had been removed. The isolated facial nuclei were processed for RNA extraction using the Invitrogen S.N.A.P.™ Total RNA Isolation Kit (Invitrogen Cat# K 1950, Carlsbad, Calif.) according to the manufacturer's directions with the following modifications: The tissue was homogenized using a rotor-stator homogenizer (Fisher) for 20 seconds. The DNA digestion step was repeated a second time following the isopropanol precipitation.

Quantitative RT-PCR analysis was carried out on the isolated RNA using primers and probes specific for rat GAPDH (M17701), Norway rat GFAP (Z48978), and Wistar rat MHC II Iα (M29311).

Based on RNA yields from serveral independent dissections with either individual nuclei, or pooled nuclei, approximately 1–1.5 μg of total RNA was extracted per facial nucleus (ranged from 0.7–2.2) using a variety of RNA extraction methods including our standard method worked out for qtPCR of mouse brain RNA. The integrity of the RNA has been confirmed by northern blot analysis using a cDNA probe for actin. Northern blot analysis showed two mRNAs for actin at 1.8 kb and 4.6 kb, which confirmed the integrity of RNA isolation.

EXAMPLE 4 mRNA Expression of Certain Markers in APP Transgenic Mice Immunized with Aβ1-42 or Fragments Thereof Transgenic mice overexpressing APP with a mutation at position 717 ($APP_{717V F}$), which are predisposed to develop Alzheimer's-like neuropathology (PDAPP mice, described in Games et al., Nature 373, 523 (1995)), were immunized with Aβ1-42 or a fragment thereof. Immunization with Aβ1-42 or a fragment thereof has been shown to prevent deposition or clear Aβ from brain tissue, with the concommittant elimination of subsequent neuronal and inflammatory degenerative changes associated with Aβ. mRNA expression of various markers was determined in Aβ-treated mice and control mice that were not treated with Aβ. The results are presented below in Table 5 as a ratio of mRNA of Aβ-treated mice to non-Aβ-treated mice. Preferred primers are shown in Table 6. As shown below, the mRNA expression of various markers increased in Aβ-treated mice. The increases observed in MCP-1, IL-10, IL-12, CD3, CD4, IgG-1, and Ig k mRNA expression are particularly compelling. Immunization with Aβ1-42 or a fragment thereof has been shown to prevent deposition or clear Aβ from brain tissue, with the concommittant elimination of subsequent neuronal and inflammatory degenerative changes associated with Aβ. Thus, the efficacy of Aβ-treatment can be assessed by comparing the mRNA expression of such markers.

TABLE 5

| Marker | Aβ1-42/ Control Hippocamp | Aβ1-42/ Control Fr cortex | Aβ1-5/ Control | Aβ1-12/ Control | Aβ40-1/ Control |
|---|---|---|---|---|---|
| MCP-1 | 2.9X | 3X | 0.75X | 0.43X | 1.31X |
| IL-10 | 15X | 116X | ND | ND | ND |
| IL-12 | 8.4X | 4.1X | ND | ND | ND |

TABLE 5-continued

| Marker | Aβ1-42/ Control Hippocamp | Aβ1-42/ Control Fr cortex | Aβ1-5/ Control | Aβ1-12/ Control | Aβ40-1/ Control |
|---|---|---|---|---|---|
| IFN-γ | 1.4X | 2.7X | .8X | .43X | 1.85X |
| CD3ϵ | 35X | 272X | ND | ND | ND |
| CD4 | 6.3X | 10.3X | 0.99X | 0.59X | 1.19X |
| IgG-1 | 0 | 300X | ND | ND | ND |
| Igk | 1.3X | 6.6X | 2.10X | 1.89X | 1.39X |

EXAMPLE 5

Increased Osteopontin mRNA Expression in APP Transgenic Mice Compared to Non-transgenic Mice Osteopontin mRNA levels were determined in PDAPP and non-transgenic mice. Preferred primers are shown in Table 6. At 2, 12 and 18 months of age, PDAPP mice had levels of osteopontin mRNA 3.41X, 6.26X and 2.65X, respectively, greater than the osteopontin mRNA levels of non-transgenic mice.

TABLE 6

| Marker | F. primer seq. | R. primer seq. | probe seq. |
|---|---|---|---|
| Osteopontin | 15F:GATTTGCTTTTGCCTGTTTGG (SEQ ID NO:34) | 81R:TGAGCTGCCAGAATCAGTCACT (SEQ ID NO:35) | 38T: TTGCCTCCTCCCTCCCGGTGA (SEQ ID NO:36) |
| VitD3-24OHase | 1164F:CCCAAGTGTGCCATTCACAAC (SEQ ID NO:37) | 1236R:TCCTTTGGGTAGCGTGTATTCA (SEQ ID NO:38) | 1186:CGGACCCTTGACAAGCCAACCGT (SEQ ID NO:39) |
| MCP-1 | 47F:GCTGGAGCATCCACGTGTT (SEQ ID NO:40) | 142R:GCCTACTCATTGGGATCATCTTG (SEQ ID NO:41) | 71T:AGCCAGATGCAGTTAACGCCCCACT (SEQ ID NO:42) |
| IL-10 | #2-294F:AGAGAAGCATGGCCCAGAAAT (SEQ ID NO:43) | #2-365R:CGCATCCTGAGGGTCTTCA (SEQ ID NO:44) | #2-317T:CTTCTCACCCAGGGAATTCAAATGCTCCT (SEQ ID NO:45) |
| IL-12 p-40, #1 | 662F:ACAGCACCAGCTTCTTCATCAG (SEQ ID NO:46) | 734R:TTCAAAGGCTTCATCTGCAAGTT (SEQ ID NO:47) | 687T:CATCATCAAACCAGACCCGCCCAA (SEQ ID NO:48) |
| #2 | 929F:ACATCTACCGAAGTCCAAGTCA (SEQ ID NO:49) | 1002R:CATGAGGAATTGTAATAGCGATCCT (SEQ ID NO:50) | 952T:AGGCGGGAATGTCTGCGTGCA (SEQ ID NO:51) |
| IFN-gamma, #1 | 378F:CAGCAACAGCAAGGCGAAA (SEQ ID NO:52) | 450R:CTGGACCTGTGGGTTGTTGAC (SEQ ID NO:53) | 398T:AGGATGCATTCATGAGTATTGCCAAGTTTGA (SEQ ID NO:54) |
| #2 | 67F:ACAATGAACGCTACACACTGCAT (SEQ ID NO:55) | 139R:CGTGGCAGTAACAGCCAGAA (SEQ ID NO:56) | 91T:TTGGCTTTGCAGCTCTTCCTCATGG (SEQ ID NO:57) |
| CD3 epsilon | 115F:GAGTTGACGTGCCCTCTAGACAG (SEQ ID NO:58) | 193R:TATCATGCTTCTGAGGCAGCTC (SEQ ID NO:59) | 140T:TGGCCATTTTTTTCCCATTTTAAGTTCTCGT (SEQ ID NO:60) |
| CD4,#1 | 359F:AGGTGGAGTTGTGGGTGTTCA (SEQ ID NO:61) | 426R:CAGGCTCTGCCCTTGCAA (SEQ ID NO:62) | 381T:AGTGACCTTCAGTCCGGGTACCAGCC (SEQ ID NO:63) |
| #2 | 388F:AGGAAAGAGGAGGTGGAGTTGTG (SEQ ID NO:64) | 465R:CAGGCTCTGCCCTTGCAA (SEQ ID NO:65) | 413T:TGTTCAAAGTGACCTTCAGTCCGGGTACC (SEQ ID NO:66) |
| IgG-1 | 134F:TGGAGGTGCACACAGCTCAG (SEQ ID NO:67) | 195R:TGAGCGGAAAGTGCTGTTGA (SEQ ID NO:68) | 155T:CTGCTCCTCCCGGGGTTGCG (SEQ ID NO:69) |
| Ig k (light chain) | 151F:GGCGTCCTGAACAGTTGGA (SEQ ID NO:70) | 219R:CGTGAGGGTGCTGCTCATG (SEQ ID NO:71) | 171T:TGATCAGGACAGCAAAGACAGCACCTACA (SEQ ID NO:72) |

TABLE 6-continued

| Marker | Amplicon |
|---|---|
| Osteopontin | gatttgcttttgcctgtttggcattgcctcctccctcccggtgaaagtgactgattctggcagctca (SEQ ID NO:73) |
| VitD3-24OHase | cccaagtgtgccattcacaactcggaacccttgacaagccaaccgttctgggtgaatacacgctacccaaagga (SEQ ID NO:74) |
| MCP-1 | gctggagcatccacgtgttggctcagccagatgcagttaacgccccactcacctgctgctactcattcaccagcaagatgatcccaatgagtaggc (SEQ ID NO:75) |
| IL-10 | agagaagcatggcccagaaatcaaggagcatttgaattccctgggtgagaagctgaagaccctcaggatgcg (SEQ ID NO:76) |
| IL-12 p40, #1 | acagcaccagcttcttcatcagggacatcatcaaaccagacccgcccaagaacttgcagatgaagcctttgaa (SEQ ID NO:77) |
| #2 | acatctaccgaagtccaatgcaaaggcgggaatgtctgcgtgcaagctcaggatcgctattacaattcctcatg (SEQ ID NO:78) |
| IFN-gamma, #1 | cagcaacagcaaggcgaaaaaggatgcattcatgagtattgccaagtttgaggtcaacaacccacaggtccag (SEQ ID NO:79) |
| #2 | acaatgaacgctacacactgcatcttggctttgcagctcttcctcatggctgtttctggctgttactgccacg (SEQ ID NO:80) |
| CD3 epsilon | gagttgacgtgccctctagacagtgacgagaacttaaaatgggaaaaaaatggccaagagctgcctcagaagcatgata (SEQ ID NO:81) |
| CD4, #1 | aggtggagttgtgggtgttcaaagtgaccttcagtccgggtaccagcctg (SEQ ID NO:82) |
| #2 | aggaaagaggaggtggagttgtgggtgttcaaagtgaccttcagtccgggtaccagcctgttgcaagggcagagcctg (SEQ ID NO:83) |
| IgG-1 | tggaggtgcacacagctcagacgcaaccccgggaggagcagttcaacagcactttccgctca (SEQ ID NO:84) |
| Ig k (light chain) | ggcgtcctgaacagttggactgatcaggacagcaaagacagcacctacagcatgagcagcaccctcacg (SEQ ID NO:85) |

While the invention has been described with reference to specific methods and embodiments, it will be appreciated that various modifications and changes may be made without departing from the invention.

It is claimed:

1. A method of selecting a compound effective in reducing inflammation associated with Alzheimer's Disease in a mammalian subject, comprising subjecting a non-human mammalian subject to a cerebral ischemic event characterized by elevation in an affected region of a marker selected from the group consisting of IL1β, TNFα, MIP-1α, GFAP, MHC IIα, MHC II Li, CD86, fractalkine and CX3CR1, administering to the test subject a test compound, selecting the test compound as effective in reducing inflammation associated with Alzheimer's Disease (AD) if an amount of the marker present in the affected region is significantly lower than an amount of marker protein present in an affected region in a control ischemic subject.

2. The method of claim 1, wherein said marker is a coding sequence and said amount of marker is measured using quantitative PCR.

3. The method of claim 1, wherein said coding sequence is mRNA present in said affected region and said measuring is by RT-PCR.

4. The method of claim 1, wherein said marker is IL1β.

5. The method of claim 1, wherein said marker is TNFα.

6. The method of claim 1, wherein said marker is MIP-1α.

7. The method of claim 1, wherein said marker is GFAP.

8. The method of claim 1, wherein said marker is CD86.

9. The method of claim 1, wherein said marker is MHC IIα.

10. The method of claim 1, wherein said marker is MHC II Li.

11. The method of claim 1, wherein said marker is fractalkine.

12. The method of claim 1, wherein said marker is CX3CR1.

13. The method of claim 1, wherein said subject is a mouse and said cerebral ischemic event is cerebral ischemia subsequent to bilateral carotid occlusion.

14. The method of claim 13, wherein said cerebral ischemic event is further characterized by gross morphological degeneration of cells in the CA1region of the hippocampus in said control subject.

15. A method of selecting a compound effective to reduce inflammation associated with Alzheimer's Disease in the central nervous system, comprising lesioning a nerve in a test non-human mammalian subject to produce a denervated cell body region characterized by elevation in an affected region of a marker protein selected from the group consisting of IL1β, TNFα, MIP-1α, GFAP, MHC IIα, MHC II Li, CD86, fractalkine and CX3CR1, administering to the test subject a test compound, selecting the test compound as effective in reducing inflammation associated with Alzheimer's Disease if an amount of the marker protein present in the denervated region is significantly lower than an amount of marker protein present in a denervated region in a control subject.

16. The method of claim 15, wherein said marker is a coding sequence and said amount of marker is measured using quantitative PCR.

17. The method of claim 16, wherein said coding sequence is mRNA present in said affected region and said measuring is by RT-PCR.

18. The method of claim 15, wherein said marker is IL1β.

19. The method of claim 15, wherein said marker is TNFα.

20. The method of claim 15, wherein said marker is MIP-1α.

21. The method of claim 15, wherein said marker is GFAP.

22. The method of claim 15, wherein said marker is CD86.

23. The method of claim 15, wherein said marker is MHC IIα.

24. The method of claim 15, wherein said marker is MHC II Li.

25. The method of claim 15, wherein said subject is a mouse and said denervated cell body region is the facial motor nucleus.

26. A method of selecting a compound effective to reduce inflammation associated with Alzheimer's Disease, comprising administering a test compound to a transgenic mouse whose genome comprises a mutant gene for amyloid precursor protein (APP), the mouse exhibiting AD-like inflammation in its central nervous system upon production of APP least one marker selected from the group consisting of osteopontin, CD86, fractalkine and CX3CR1, measuring the amount of mRNA in the test animal central nervous system specific for a marker selected from the group consisting of osteopontin, CD86, fractalkine and CX3CR1, selecting the compound as effective to reduce inflammation associated with Alzheimer's Disease if the amount said marker is significantly less than an amount said marker measured in a corresponding central nervous system sample from a control transgenic animal.

27. The method of claim 26, wherein said measuring is effected by reverse transcription polymerase chain reaction (RT-PCR) of an mRNA corresponding to said marker.

28. The method of claim 26, wherein said transgenic mouse is a PDAPP mouse.

29. The method of claim 26, wherein said marker is CD86.

30. The method of claim 26, wherein said marker is fractalkine.

31. The method of claim 26, wherein said marker is CX3CR1.

32. The method of claim 26, wherein said marker is osteopontin.

33. The method of claim 26, wherein said measuring is effected by measuring an amount of antibody selective for said marker.

34. A method of selecting a compound effective to reduce inflammation associated with Alzheimer's Disease, comprising administering a test compound to a transgenic mouse whose genome comprises a mutant gene for amyloid precursor protein (APP), the mouse exhibiting amyloid plaque formation in its central nervous system, comprising measuring in the test animal central nervous system the amount of marker selected from the group consisting of osteopontin, CD86, fractalkine and CX3CR1, selecting the compound as effective to reduce inflammation associated with Alzheimer's Disease if the amount said marker is significantly less than an amount of the marker measured in a corresponding central nervous system sample from a control transgenic animal.

35. The method of claim 34, wherein said marker is an mRNA molecule and said measuring is effected by reverse transcription polymerase chain reaction (RT-PCR).

36. The method of claim 34, wherein said transgenic mouse is a PDAPP mouse.

37. The method of claim 34, wherein said marker is CD86.

38. The method of claim 34, wherein said marker is fractalkine.

39. The method of claim 34, wherein said marker is CX3CR1.

40. The method of claim 34, wherein said marker is osteopontin.

41. A method of monitoring inflammation associated with Alzheimer's Disease, comprising administering Aβ42 or a fragment thereof to a transgenic mouse whose genome comprises a mutant gene for amyloid precursor protein (APP), the mouse exhibiting AD-like inflammation in its central nervous system upon production of APP, wherein said AD-like inflammation includes induction of at least one marker selected from the group consisting of IL1β, TNFα, MIP-1α, GFAP, MHC IIα, MHC II Li, osteopontin, CD86, fractalkine and CX3CR1, measuring the amount of mRNA or protein in the transgenic mouse central nervous system specific for at least one marker selected from the group;

measuring the amount of mRNA or protein specific for the at least one marker in a control transgenic mouse central nervous system; wherein a difference in level of the marker indicates the administered Aβ42 or a fragment affects inflammation in the transgenic mouse to which the Aβ42 or a fragment was administered.

42. The method of claim 41, wherein the at least one marker is an mRNA molecule and the measuring steps are effected by reverse transcription polymerase chain reaction (RT-PCR).

43. The method of claim 41, wherein said transgenic mouse is a PDAPP mouse.

* * * * *